United States Patent
Lorenz et al.

(10) Patent No.: US 6,991,660 B2
(45) Date of Patent: *Jan. 31, 2006

(54) COMPOSITION FOR THE DYEING OF HUMAN HAIR

(75) Inventors: Heribert Lorenz, Gross-Bieberau (DE); Klaus Kaffenberger, Alsbach-Haehnlein (DE); Bernd Noecker, Ober-Ramstadt (DE); Ruediger Wilz, Pfungstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/642,917

(22) Filed: Aug. 18, 2003

(65) Prior Publication Data

US 2004/0107514 A1    Jun. 10, 2004

(30) Foreign Application Priority Data

Dec. 10, 2002 (DE) .............................. 102 57 490

(51) Int. Cl.
 *A16K 7/13* (2006.01)
(52) U.S. Cl. .................. 8/405; 8/406; 8/510; 8/411; 8/412; 8/423
(58) Field of Classification Search ............... 8/405, 8/406, 410, 411, 412, 421, 423
See application file for complete search history.

(56) References Cited

U.S. PATENT DOCUMENTS

| | | | | |
|---|---|---|---|---|
| 4,003,699 A | * | 1/1977 | Rose et al. ............. | 8/409 |
| 4,865,619 A | * | 9/1989 | Junino et al. ........... | 8/412 |
| 5,015,260 A | * | 5/1991 | Tamura et al. .......... | 8/408 |
| 5,104,414 A | * | 4/1992 | Tamura et al. .......... | 8/408 |
| 5,578,087 A | * | 11/1996 | Audousset et al. ..... | 8/409 |
| 5,693,101 A | * | 12/1997 | Audousset et al. ..... | 8/408 |

FOREIGN PATENT DOCUMENTS

| | | | |
|---|---|---|---|
| DE | 24 47 017 C2 | | 7/1987 |
| DE | 019834657 C1 | * | 2/2000 |
| DE | 20017642 U1 | * | 12/2000 |
| DE | 200 17 642 U | | 1/2001 |
| DE | 100 51 034 A1 | | 4/2002 |
| EP | 1 378 228 A1 | | 1/2004 |

OTHER PUBLICATIONS

European Search Report dated Jan. 7, 2004 for Application No. EP 03 01 5935.

* cited by examiner

*Primary Examiner*—Eisa Elhilo
(74) *Attorney, Agent, or Firm*—Norris McLaughlin & Marcus PA

(57) ABSTRACT

Hair dyeing composition on the basis of an oxidation dyestuff precursor reacting with peroxide, comprising at least one developing and/or coupling substance selected from the group a) 3-chloro-p-aminophenol and/or 2-chloro-p-aminophenol,
b) 2-methyl-5-aminophenol, 2-methyl-5-hydroxyethyl aminophenol, 2-methyl-5-γ-hydroxypropyl aminophenol, 2-methyl-5-methyl aminophenol, 2-methyl-5-ethyl aminophenol, 2-methoxy-5-aminophenol, 2-methyl-4-methoxy-5-aminophenol and/or 2-methyl-4-methoxy-5-hydroxyethyl aminophenol and
c) 1-methoxy-2,4-diaminobenzene, 1-β-hydroxyethyloxy-2,4-diaminobenzene, 1-(1,2-dihydroxypropyloxy)-2,4-diaminobenzene, 1-methoxy-2-amino-4-β-hydroxyethyl aminobenzene, 1,3-bis-(2,4-diaminophenoxy)-propane, 2,4-diamino-5-methylphenetol and/or 1-β-hydroxyethyloxy-5-methyl-2,4-diaminobenzene.

2 Claims, No Drawings

COMPOSITION FOR THE DYEING OF HUMAN HAIR

The present invention concerns a composition for the dyeing of human hair on the basis of an oxidation dyestuff precursor system reacting with peroxide which provides long-lasting, intensive colors either used as such, or which can be used to obtain further shades in combination with additional developing and/or coupling agents and which does not damage the hair even upon repeated application within short intervals.

The developing substances still most frequently used in hair dyeing compositions are 1,4-diaminobenzene (p-phenylenediamine) and 1-methyl-2,5-diaminobenzene (p-toluylenediamine). Although incorporation of these substances largely fulfills the user's color wishes, there are still shades that cannot be completely achieved by the use thereof.

Proposals have also been made to close this gap by the use of alternative developing substances. To a limited degree this is possible with the use of tetraaminopyrimidine or 2-(2,5-diaminophenyl)ethanol (see EP-A 7537 and EP-B 400 330); however, it is then necessary to accept reduced color intensity in other shades. A further satisfactory solution of this problem is disclosed in EP-A 615 743, with the use of 2-(2'-hydroxyethyl amino)-5-aminotoluene or the water-soluble salts thereof, as a component of oxidation hair dye compositions.

However, to the present it has not been possible to achieve strong colorations in the range of gray-red or in the range of brown by this means.

The invention starts from the task of counteracting this deficiency and providing an oxidation dyestuff composition which achieves intensive, glossy colorations, especially in the range of brown and gray-red, and which leaves the hair without damage even upon repeated application within short periods of time.

This task is solved when such a hair dyeing composition comprises an oxidation dyestuff system reacting with peroxide which is selected from a) 3-chloro-p-aminophenol and/or 2-chloro-p-aminophenol, b) 3-(N-methyl-N-hydroxyethyl amino)-phenol, 3-morpholinophenol, 3-(N-hydroxyethyl amino)-phenol and/or 3-(N-hydroxypropyl amino)-phenol and c) 2,4-diaminobenzene, 1-methoxy-2,4-diamino-benzene, 1-β-hydroxyethyloxy-2,4-diaminobenzene, 1-methoxy-2-amino-4-β-hydroxyethyl aminobenzene, 1,3-bis-(2,4-diaminophenoxy)-propane, 2,4-diamino-5-methyl-phenetol, 1-β-hydroxyethyloxy-5-methyl-2,4-diaminobenzene and/or 5-chloro-2,4-diaminobenzene.

After oxidation with peroxide, use of these compositions on the basis of a customary carrier provides very expressive, intensive, long-lasting hair colorations, especially in the range of brown and gray-red, which can be varied to achieve further shades by the addition of the respective further developing and coupling substances.

In addition to the named developing and coupling substances it is also possible to incorporate further substances of this type.

These are, for example, 1-methoxy-2-amino4-(β-hydroxyethyl amino)benzene, 2-amino-3-hydroxypyridine, 3-amino-2-methyl amino-6-methoxypyridine, resorcinol, 2-methyl resorcinol, 4-chlororecorcinol, 1,3-diaminobenzene, 1,6-dihydroxy-naphthaline, 1,7-dihydroxy-naphthaline, p-phenylenediamine, p-toluylenediamine, 2,6-dimethyl-p-phenylenediamine, 2-hydroxymethyl-p-phenylenediamine, 2-hydroxyethyl-p-phenylenediamine, 2-n-propyl-p-phenylenediamine, N,N-bis(β-hydroxyethyl)-p-phenylenediamine, N-methoxyethyl-p-phenylenediamine and/or 5-chloro-2-hydroxyethyl-p-phenylenediamine or the water-soluble salts thereof.

The total concentration of the developing substances customarily ranges between about 0.05% and 5%, preferably 0.1% and 4%, in particular 0.25% to 0.5% and 2.5% to 3% by weight, calculated to the total hair dyeing composition (excluding the oxidation agent), whereby these figures are always related to the proportion of free base. The preferred weight proportion of the developing substances to the additional developing and coupling substances ranges between about 1:8 to 8:1, preferably about 1:5 to 5:1, in particular 1:2 to 2:1.

In the hair dyeing compositions according to the invention, the coupling substance(s) as reaction partners of the developing substance(s) are present in approximately the same molecular proportions as the developing substances, i.e. in amounts from 0.05% to 5.0%, preferably 0.1% to 4%, in particular 0.5% to 3% by weight, calculated to the total composition (excluding the oxidizing agent), whereby these figures are always related to the proportion of free base.

If desired, the compositions according to the invention can also contain so-called shading agents for precise adjustment of the desired shade, in particular direct-acting dyestuffs.

Such shading agents are, for example, nitro dyestuffs such as 2-amino4,6-dinitrophenol, 2-amino4-nitrophenol, 2-amino-6-chloro4-nitrophenol, etc., preferably in amounts from about 0.05% to 2.5%, in particular 0.1% to 1% by weight of the dyestuff composition (excluding the oxidizing agent).

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2% to 6% by weight.

However, the use of other peroxides such as urea peroxide and melamine peroxide is also possible.

The pH-value of the ready-to-use hair dyeing composition, i.e. after mixing with peroxide, can be in a slightly acidic range, i.e. from 5.5 to 6.9, as well as in the neutral or alkaline range, i.e. between pH 7.1 and 10.

In the following, various Examples are used to illustrate the invention.

| | |
|---|---|
| Stearyl alcohol | 8.0 |
| | (% by wt.) |
| Coco fatty acid monoethanolamide | 4.5 |
| 1.2-Propanediol mono/distearate | 1.3 |
| Coco fatty alcohol polyglycol ether | 4.0 |
| Sodium lauryl sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ascorbic acid | 0.2 |
| Perfume | 0.4 |
| Ammonia, 25% | 1.0 |

-continued

| | | |
|---|---|---|
| Ammonium chloride | 0.5 | |
| Panthenol | 0.8 | |
| Water | ad | |
| | 100.00 | |

The oxidation dyestuff combinations according to the invention were incorporated into this carrier, whereby the water content was reduced accordingly.

The colorations were carried out on wool patches and strands of bleached human, hair by application of a 1:1 mixture of a dyestuff precursor and a 6% hydrogen peroxide solution (pH-value of the mixture: 9.8) with twenty minutes processing at room temperature, subsequent rinsing and drying.

The following colorations were achieved:

Example 1:

| 0.41 | (% by wt.) | 3-Chloro-p-aminophenol HCL |
|---|---|---|
| 0.17 | | 3-(N-hydroxyethyl amino)-phenol |
| 0.31 | | 1-Methoxy-2-amino-4-β-hydroxy-ethyl aminobenzene $H_2SO_4$ |
| Coloration: | Intensive gray-red. | |

Example 2:

| 0.41 | (% by wt.) | 3-Chloro-p-aminophenol HCL |
|---|---|---|
| 0.20 | | 3-Morpholinophenol |
| 0.27 | | 1-β-Hydroxyethyloxy-2.4-diaminobenzene HCL |
| Coloration: | Gray-red. | |

Example 3:

| 0.41 | (% by wt.) | 3-Chloro-p-aminophenol HCL |
|---|---|---|
| 0.16 | | 2-Chloro-p-aminophenol |
| 0.19 | | 3-(N-methyl-N-hydroxyethyl amino)-phenol |
| 0.12 | | 2.4-Diaminobenzene |
| Coloration: | Gray-brown. | |

Example 4:

| 0.41 | (% by wt.) | 3-Chloro-p-aminophenol HCL |
|---|---|---|
| 0.17 | | 3-(N-Hydroxyethyl amino)-phenol |
| 0.49 | | 1.3-bis-(2.4-Diaminophenoxy)-propane 4 HCL |
| Coloration: | Brown-violet. | |

Example 5:

| 0.32 | (% by wt.) | 2-Chloro-p-aminophenol |
|---|---|---|
| 0.17 | | 3-(N-Hydroxyethyl amino)-phenol |
| 0.16 | | 5-Chloro-2.4-diaminobenzene |
| Coloration: | Gold-brown. | |

The invention claimed is:

1. A hair dyeing composition on the basis of an oxidation dyestuff precursor reacting with peroxide, comprising developing and/or coupling substances, wherein said substances consist of:
   a) at least one developing and/or coupling substance selected from the group consisting of 3-chloro-p-aminophenol and 2-chloro-p-aminophenol;
   b) at least one developing and/or coupling substance selected from the group consisting of 3-(N-methyl-N-hydroxyethyl amino)-phenol, 3-morpholinophenol, 3-(N-hydroxyethyl amino)-phenol and 3-(N-hydroxypropyl amino)-phenol and
   c) at least one developing and/or coupling substance selected from the group consisting of 2,3-diaminobenzene, 1-methoxy-2,4,diaminobenzene, 1-β-hydroxyethyloxy-2,4,-diaminobenzene, 1-methoxy-2-amino-4-β-hydroxy-ethyl aminobenzene, 1,3-bis-(2,4-diaminophenoxy)-propane, 2,4-diamino-5-methylphenetol, 1-β-hydroxy-ethyloxy-5-methyl-2,4-diaminobenzene and 5-chloro-2,4,-diaminobenzene.

2. A hair dyeing composition on the basis of an oxidation dyestuff precursor reacting with peroxide, comprising developing and/or coupling substances, wherein said substances consist of:
   a) at least one developing and/or coupling substance selected from the group consisting of 3-chloro-p-aminophenol and 2-chloro-p-aminophenol;
   b) at least one developing and/or coupling substance selected from the group consisting of 3-(N-methyl-N-hydroxyethyl amino)-phenol, 3-morpholinophenol, 3-(N-hydroxyethyl amino)-phenol and 3-(N-hydroxypropyl amino)-phenol;
   c) at least one developing and/or coupling substance selected from the group consisting or 2,3-diaminobenzene, 1-methoxy-2,4-diaminobenzne, 1-β-hydroxyethyloxy-2,4-diaminobenzene, 1-methoxy-2-amino-4-β-hydroxy-ethylaminobenzene, 1,3-bis-(2,4-diaminophenoxy)-propane, 2,4-diamino-5-methylphenetol, 1-β-hydroxy-ethyloxy-5-methyl-2,4-diaminobenzene and 5-chloro-2,4-diaminobenzene and
   d) at least one developing and/or coupling substance selected from the group consisting of 2-amino-3-hydroxypyridine, 3-amino-2-methylamino-6-methoxypyridine, resorcinol, 2-methyl resorcinol, 4-chlororesorcinol, 1,3-diaminobenzene, 1,6-dihydroxynapthalene, 1,7-dihydroxy-napthalene, p-phenylenediamine, p-toluylenediamine, 2,6-dimethyl-p-phenylenediamine, 2-hydroxymethyl-p-phenylenediamine, N,N-bis(β-hydroxyl)-p-phenylenediamine, N-methoxyethyl-p-phenylenediamine, 5-chloro-2-hydroxyethyl-p-phenylenediamine and water-soluble salts thereof.

* * * * *